United States Patent
Chenoweth

(10) Patent No.: US 10,591,461 B2
(45) Date of Patent: Mar. 17, 2020

(54) METHOD OF DRUG DESIGN AND OPTIMISATION UTILIZING STEREOCHEMICAL MIMICRY

(71) Applicant: The Trustees of the University of Pennsylvania, Philadelphia, PA (US)

(72) Inventor: David M. Chenoweth, Philadelphia, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 0 days.

(21) Appl. No.: 16/097,148

(22) PCT Filed: Apr. 27, 2017

(86) PCT No.: PCT/US2017/029956
§ 371 (c)(1),
(2) Date: Oct. 26, 2018

(87) PCT Pub. No.: WO2017/189920
PCT Pub. Date: Nov. 2, 2017

(65) Prior Publication Data
US 2019/0154662 A1    May 23, 2019

Related U.S. Application Data

(60) Provisional application No. 62/328,986, filed on Apr. 28, 2016, provisional application No. 62/328,961, filed on Apr. 28, 2016.

(51) Int. Cl.
| | | |
|---|---|---|
| G01N 33/50 | (2006.01) |
| C07D 403/06 | (2006.01) |
| G01N 33/68 | (2006.01) |
| C07D 231/04 | (2006.01) |
| C07K 5/10 | (2006.01) |
| A61K 38/00 | (2006.01) |

(52) U.S. Cl.
CPC ....... *G01N 33/5008* (2013.01); *C07D 231/04* (2013.01); *C07D 403/06* (2013.01); *C07K 5/10* (2013.01); *G01N 33/6893* (2013.01); *A61K 38/00* (2013.01)

(58) Field of Classification Search
None
See application file for complete search history.

(56) References Cited

U.S. PATENT DOCUMENTS

2004/0236519 A1    11/2004    Marshall et al.

FOREIGN PATENT DOCUMENTS

| WO | WO 2011/044089 | 4/2011 |
| WO | WO 2017/189920 | 11/2017 |

OTHER PUBLICATIONS

Zhang et al., Angewandte Chem. Int. Ed., vol. 54, p. 10826-10832 (2015).

*Primary Examiner* — Christopher M Gross
(74) *Attorney, Agent, or Firm* — Morgan, Lewis & Bockius LLP; Robin M. Silva

(57) ABSTRACT

The invention relates to a method of designing or optimizing a drug candidate by making stereodynamic derivatives as well as novel derivatives of Glyx-13 with improved biological and pharmacological properties.

6 Claims, 7 Drawing Sheets

Rapastinel (GLYX-13)

Thr-Pro-Pro-Thr-NH$_2$

Glyx-1

Glyx-2

Glyx-3

X = N, B or any atom capable of replacing the stereocenter

METHOD OF DRUG DESIGN AND OPTIMISATION UTILIZING STEREOCHEMICAL MIMICRY

CROSS REFERENCE TO RELATED APPLICATIONS

This application claims the benefit under 35 U.S.C. § 119(e) of U.S. Provisional Application No. 62/328,961 filed on Apr. 28, 2016 and U.S. Provisional Application No. 62/328,986 filed Apr. 28, 2016, both of which are incorporated herein by reference in their entireties for all purposes.

BACKGROUND OF THE INVENTION

Stereochemistry plays an important role in biological functions and drug design. In many instances, one stereoisomer of a compound may have positive effects on the human body while another stereoisomer may not work at all or may even be toxic. In a well-known example, one stereoisomer of ibuprofen works well as a pain killer while the other stereoisomer is completely ineffective at treating pain. In another well-known example, the drug thalidomide was widely used to suppress morning sickness in pregnant women in the 1950s. At the time, the drug was prescribed as a racemic mixture (i.e. a 50:50 mixture of the two stereoisomers). In this case, while one stereoisomer worked on controlling morning sickness, the other stereoisomer caused serious birth defects. As a result, a great deal of effort has been spent on devising methods to synthesize compounds that are purely one stereoisomer.

The reason stereoisomers may have such dramatically different biological effects is because they have very different 3-dimensional conformations. In the context of structure-based drug design, it is well-known in the art that proteins are often enantioselective towards their binding partners. Binding affinity is strongest when two binding partners have complementary geometry. Thus, when designing molecules to interact with biological targets, stereoselectivity is often a major consideration. As researchers expand their exploration of the chemical structure space for potential drug candidates, chirality is increasingly becoming a focal point.

One group of potential drug candidates is the Glyxin family, which are small peptides that mimic the biological activity of the monoclonal antibody B6B21. Importantly, monoclonal antibody B6B21 was found to act as a partial agonist on the glycine site of the NMDA receptor and NMDA partial agonists are currently being pursued as drugs to protect against stroke-induced neuronal damages and to alleviate neuropathic pain. The NMDA receptor is also involved in many cognitive functions, such as learning, memory, depression, and schizophrenia. Among the Glyxins, Glyx-13, also known as rapastinel, is one of the most effective leads.

While Glyx-13 is a great drug candidate, it does have at least one problem—it has to be injected in order to be administered. This is because of the poor bioavailability and enzymatic degradation it undergoes in the body.

Therefore, there exists a need for novel methods to manipulate the chiral centers of molecules. Such methods may be quite useful for designing and optimizing drug candidates, including derivatives of Glyx-13 with improved or optimized pharmacological properties in conjunction with optimized biological activity.

BRIEF SUMMARY OF THE INVENTION

Accordingly, the present invention provides a method of designing or optimizing a drug candidate by making stereodynamic derivatives as well as novel derivatives of Glyx-13 with improved biological and pharmacological properties.

In one aspect, the present invention is directed to a method of designing or optimizing a drug candidate by replacing a chiral carbon of a chiral center with a nitrogen atom so as to render the chiral center stereodynamic.

In another, the present invention is directed to a method of synthesizing a stereo-mimetic compound.

Other aspects and advantages of the present invention will be apparent from the following detailed descriptions, drawings, and the appended claims.

In another aspect, derivatives of Glyx-13 in accordance with the present invention generally has one or both of its proline residues replaced with a stereo-mimic having the following general formula:

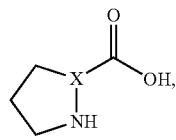

wherein X is nitrogen, boron, or any atom capable of replacing the stereocenter.

More broadly, any derivative, analog, substructure, or mimic of Glyxins or Glyx-13 containing a proline or proline derivative may have the stereogenic or alpha-carbon atom replaced by a nitrogen atom to mimic the stereochemistry or tune the properties of the parent compound.

In a preferred embodiment, derivatives of Glyx-13 includes Glyx-1 having the following chemical structure:

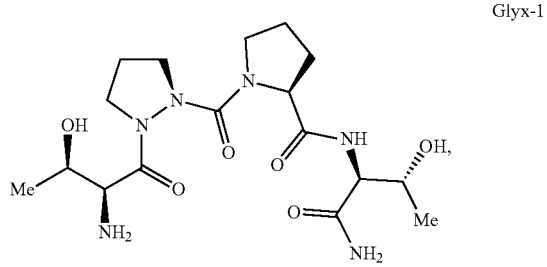

Glyx-1

Glyx-2, having the following chemical structure:

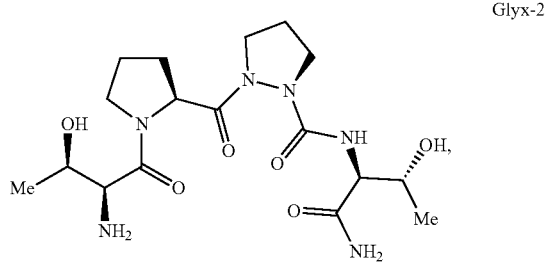

Glyx-2 and Glyx-3 having the following chemical formula:

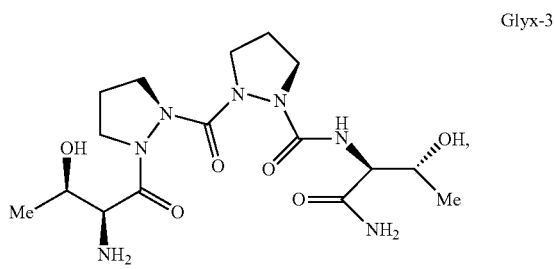

Glyx-3

Other aspects and advantages of the present invention will be apparent from the following detailed descriptions, drawings, and the appended claims.

DETAILED DESCRIPTION OF THE INVENTION

1. Introduction

Figure 1:
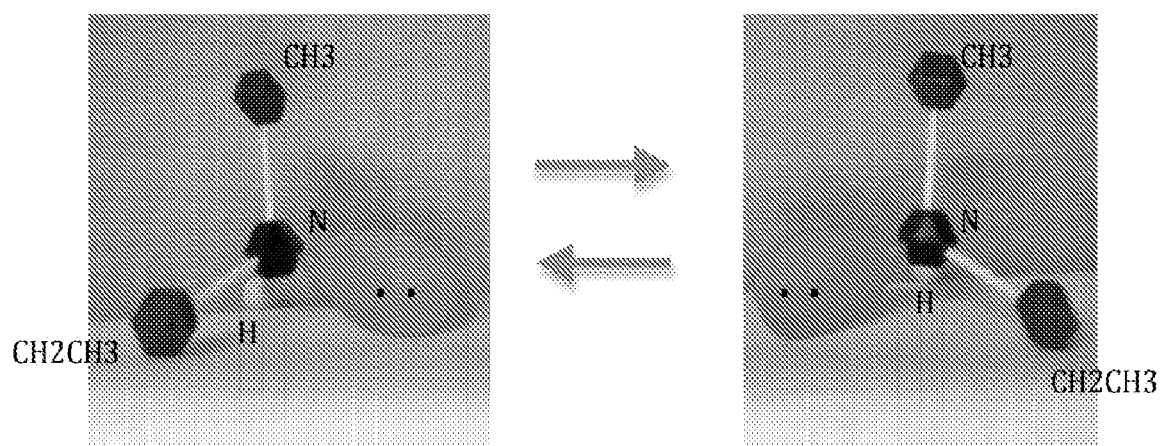
FIG. 1 illustrates the phenomenon of nitrogen inversion.

A stereocenter or a chiral center is an atom with three or more different substituents where interchanging two of them will lead to a different stereoisomer. Tetravalent carbon with four different substituents is the prototypical stereocenter. However, nitrogen with three different substituents and a lone pair also has the potential to be a stereocenter because two stereoisomeric configurations may be formed depending on which side of the symmetry plane the lone pair is located. But when the lone pair is capable of oscillating between the symmetry plane, a phenomenon called nitrogen inversion happens (see FIG. 1). Nitrogen stereocenters that undergo nitrogen inversion cannot maintain a stable stereoisomeric configuration. They are referred to as being stereodynamic and not true stereocenters. In the context of the present invention, compounds that incorporate stereodynamic chiral centers are referred to as stereodynamic mimics. The idea of replacing stable stereocenters with stereodynamic ones is herein referred to as stereomimicry.

As noted above, the chirality conferred by carbon stereocenters plays important roles in biomolecular systems. For example, all natural amino acids except for glycine have a stereocenter at α-carbon position. In nature, proteins are generally made of L-amino acids. Replacing L-amino acids with D-amino acids typically introduces local conformational constraints. Such change of chirality has been utilized as a tool in protein design. However, the ramification of replacing a stable chiral center with a stereodynamic one in the context of drug design was not known.

Using Glyxins as examples, the present invention demonstrates that stereomimicry can indeed improve the pharmacological properties of drug candidates.

Glyxins are a family of small peptides that mimic the biological activity of the monoclonal antibody B6B21, which was found to act as a partial agonist on the glycine site of the NMDA receptor (Drug Discovery Today, Vol. 7, No. 13 Jul. 2002, pp 690-691, the entire content of which is incorporated herein by reference). NMDA partial agonists are currently being pursued as drugs to protect against stroke-induced neuronal damages and to alleviate neuropathic pain. The NMDA receptor is involved in many cognitive functions, such as learning, memory, depression, and schizophrenia. Among the Glyxins, U.S. Pat. No. 8,492,340 to Joseph Moskal teaches methods for treating depression and other related diseases using Glyx-13, also known as rapastinel (the entire content of U.S. Pat. No. 8,492,340 is incorporated herein by reference, with particular reference to the formulations and treatment therein).

Figure 2:
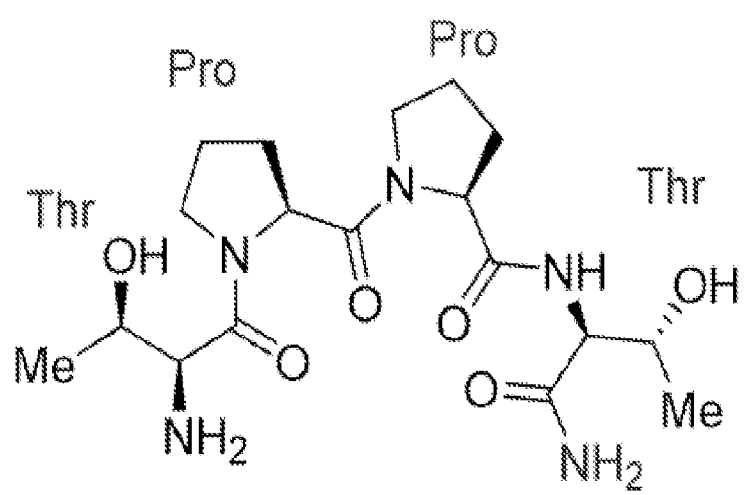
FIG. 2 shows the structure of Glyx-13 also referred to as Rapastinel.
Figure 3:
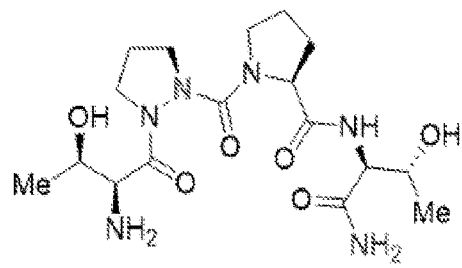
FIG. 3 shows the structures of AzaPro derivatives, Glyx-1 (upper left), Glyx-2 (upper right), and Glyx-3 (lower left), and a general formula for a stereodynamic proline residue (lower right).
Figure 3:
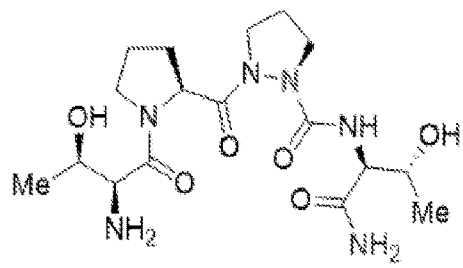
Figure 3:
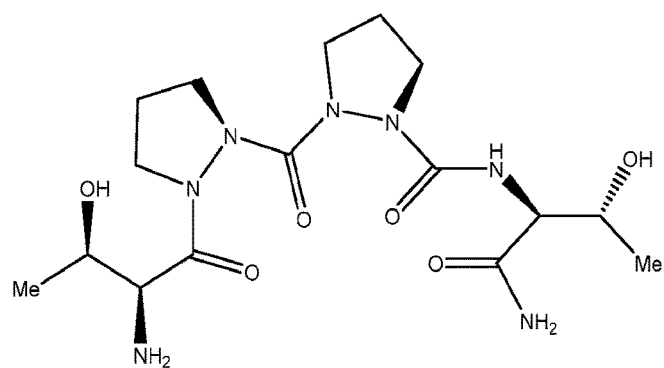
Figure 3:
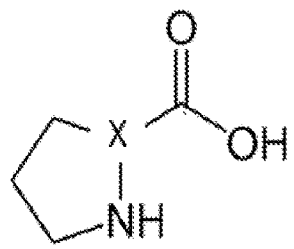

Rapastinel is a tetrapeptide having the sequence Thr-Pro-Pro-Thr-$NH_2$ (see FIG. 2). Azaproline had previously been demonstrated to be stereodynamic (Angew Chem Int Ed Engl. 2015 Sep. 7; 54(37):10826-32, the entire content of which is incorporated herein by reference). By substituting the prolines of Glyx-13 with azaproline, stereodynamic mimics of Glyx-13, Glyx-1, Glyx-2 and Glyx-3, are generated (FIG. 3). As will be shown in the examples below, both of these stereodynamic mimics are found to be more effective than the parent compound Glyx-13. Moreover, rapastinel has been found to be an antidepressant and has been Fast Tracked by the FDA as an adjunctive therapy in treatment-resistant major depressive disorder, and the drug has also received a Breakthrough Therapy designation by the FDA.

While Glyx-13 is a great drug candidate, it does have at least one problem—it has to be injected in order to be administered. This is because of the poor bioavailability and enzymatic degradation it undergoes in the body. Therefore, there still exists a need for derivatives of Glyx-13 with improved or optimized pharmacological properties in conjunction with optimized biological activity.

Accordingly, the present invention describes a novel stereomimicry-based strategy for designing, screening, and optimizing drug leads, including Glyx-13, as will be described below.

In addition, included in the definition of the compounds of the invention are polymorphs, homologs, hydrates, solvates, free bases and/or suitable salt forms.

2. Stereomimicry-Based Strategy for Designing and Optimizing Drug Leads

In one aspect, the present invention provides a general method of utilizing stereomimicry to design and/or optimize the biological effects of a drug candidate. Methods in accordance with this aspect of the invention will generally include the steps of providing a test compound having one or more stable chiral center(s); replacing at least one stable chiral center with a stereodynamic center to generate a stereodynamic mimic; and evaluating the stereodynamic mimic for a desired biological or pharmacological activity.

Candidate Agents

Accordingly, the present invention is directed to methods of stereo-optimization of candidate agents for use in therapeutic applications. "Candidate agents", or "test compounds" can be small organic molecules, peptides, proteins, nucleic acids, or an analog or mimetic thereof, as more fully outlined below. When the goal is to optimize a lead compound, the method will begin with a test compound that is a lead compound for at least one disease indication. This compound will be the reference lead compound. Preferably, the reference lead compound contains at least one chiral amino acid residue, more preferably, at least one amino acid residue is proline.

Next, with the reference lead compound as a template, a plurality of stereodynamic mimics are generated by replacing one or more of the chiral atoms with a stereodynamic atom. A chiral atom is one with three or more different substituents attached to it that can maintain a stable stereoisomeric configuration. Examples of a chiral atom may include the α-carbon of a chiral amino acid residue, but are not limited thereto. A stereodynamic atom is one that has three or more different substituents attached to it but is capable of oscillating between the two stereoisomeric configurations. One example of a stereodynamic atom may include a nitrogen atom with three different substituents and a constrained lone pair that can oscillate between the two sides of the symmetry plane. In general, any tertiary amine with a low inversion barrier could be advantageously used. Other stereodynamic atom may include boron or any atom capable of replacing the stereocenter. FIG. 3 (lower right) shows an exemplary formula for proline where the chiral α-carbon position can be replaced with N, B, or any other atom that is capable of replacing the stereocenter.

Next, each of the stereodynamic mimics is evaluated against the reference compound for its biological or pharmacological activity. Those skilled in the art will understand that evaluation of the mimetic compounds will be done using appropriate in vitro or in vivo assays established for the disease indication and the reference compound as more fully outlined below.

Finally, based on the evaluation, stereodynamic mimics that performed better than the reference compound will be selected as the new and improved lead compounds, or as final molecules to move into preclinical testing.

By "candidate agent", "candidate bioactive agent" or "candidate drugs" or grammatical equivalents herein is meant any molecule, e.g. proteins (which herein includes proteins, polypeptides, and peptides), small organic or inorganic molecules, polysaccharides, polynucleotides, etc. which are to be tested. Candidate agents encompass numerous chemical classes. In a preferred embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

Candidate agents are obtained from a wide variety of sources, as will be appreciated by those in the art, including libraries of synthetic or natural compounds. As will be appreciated by those in the art, the present invention provides a rapid and easy method for screening any library of candidate agents, including the wide variety of known combinatorial chemistry-type libraries.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In some embodiments, the stereochemical alterations are done on physiologically active peptides. More than 7000 naturally occurring peptides have been identified with a wide variety of biochemical roles, including hormones, neurotransmitters, growth factors, ion channel ligands and anti-infectives. See Fosgerau et al., Drug Development Today 20(1):122 (2015), herein incorporated by reference in its entirety.

In particular, the stereochemical alterations are done on peptide drugs, as are available and known in the art, including both those already approved by the FDA and those in testing, such as Glyx-13. For example, there are currently more than 60 FDA-approved peptides on the market, with 140 in clinical trials and more than 500 in preclinical testing.

In some embodiments, peptides active against or with GLP-1 (particularly GLP-1 agonists that find use in the treatment of diabetes, particularly type 2 diabetes, as well as obesity) are altered using the methodologies of the present invention; see Table 1 of Fosgerau et al., Drug Development Today 20(1):122 (2015), herein incorporated by reference in its entirety, as well as the sequences of those peptides shown in Table 1.

In some embodiments, the methods of the invention are used in altering antimicrobial peptides. Antimicrobial peptides can be used such as those shown in Table 1 of Fox, Nature Biotechnology 31(5):379 (2013), incorporated by reference herein with the rest of the publication in its entirety. Another group of antimicrobial peptides that can be optimized using the methods of the invention include the defensins, cecropins, maginins, as well as glycine rich peptides, and others discussed in Otvos, CMLS (Cell. Mol. Life Sci.) 59(2002) 1138-1150, hereby incorporated by reference in its entirety and for the names and sequences of a number of proline containing peptides, including thanatin, brevinins, moricin, drosocin, formaecin 1, pyrrhocoricin, apidaecin 1a, PR-39, Bac-5, penaeidin-2, buforin II, diptericin, cathelicidins, prophenins, and others mentioned throughout as well as shown in Tables 1 and 2.

In many embodiments, suitable peptide drugs or peptide drug candidates for use in the methods of the invention are those that contain one or more proline residues. These include Byetta, Symlin, Firazyr, Kalbitor, Firmagon and Natrecor.

In a preferred embodiment, the candidate bioactive agents are naturally occurring proteins or fragments of naturally occurring proteins. Thus, for example, cellular extracts containing proteins, or random or directed digests of proteinaceous cellular extracts, may be attached to beads as is more fully described below. In this way libraries of procaryotic and eucaryotic proteins may be made for screening against any number of targets. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 2 to about 50 amino acids, with from about 5 to about 30 amino acids being preferred and from about 8 to about 20 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In a preferred embodiment, candidate agents are synthetic compounds, and in particular, synthetic compounds being tested for drug activity, or those that have already been shown to have biological activity, e.g. drugs. Any number of techniques are available for the random and directed synthesis of a wide variety of organic compounds and biomolecules, including expression of randomized oligonucleotides.

Alternatively, a preferred embodiment utilizes libraries of natural compounds in the form of bacterial, fungal, plant and animal extracts that are available or readily produced.

Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In a preferred embodiment, candidate bioactive agents include proteins, nucleic acids, and chemical moieties.

The library should provide a sufficiently structurally diverse population of randomized agents to effect a probabilistically sufficient range of diversity to allow binding to a particular target. Accordingly, an interaction library must be large enough so that at least one of its members will have a structure that gives it affinity for the target. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$-$10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$-$10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

Assays

As will be appreciated by those in the art, the assays to determine biological activity will depend on the desired functionality. In many cases, the first assay will be a binding assay between the candidate agent and its intended target, generally a protein, to determine whether or not the stereo-optimized agent still binds (and frequently, with what affinity) to its intended target. Binding assays are known in the art and include ELISAs and Biacore assays, and other solid support based assays (including, for example, microarrays as well as bead based assays). In some cases, an initial binding assay is optional, e.g. need not be done; rather, the first assay can also be a biochemical assay to determine biochemical activity.

In addition to traditional binding assays, biochemical assays, generally in vitro, can also be done to determine biochemical efficacy.

In some cases, cell based biochemical assays can be done. This can be done using mammalian cell lines, for example, that have particular biochemical read outs indicative of activity. In some embodiments, for example to determine antimicrobial activity, these cell based assays are with the microbes for which activity is desired.

In some cases, additional in vivo animal model assays can be done, again as will be appreciated by those in the art and as determined by the particular disease indication of interest.

A general approach to identifying peptides that find use as the starting materials for the stereochemical alterations of the invention is outlined in Uhlig et al., EuPA Open Proteomics 4 (2014) 58-69, hereby incorporated by reference in its entirety, specifically including sections 3.1, 3.2, 3.3 and 6.

When the goal is to design or identify a new lead compound, the method may start with one or more test compounds, preferably a library of test compounds, each containing at least one stable chiral center and/or stereodynamic mimics of said chiral compound(s).

Library of test compounds may be obtained from commercial sources or generated using any conventional means known in the art. Preferably, the library includes a plurality of stereodynamic mimics of chiral compounds that either have known biological activities or is expected to have biological activities.

As used in the context of the present invention, the term "biological activity" refers to a measurable effect caused by a compound under evaluation.

Starting with the one or more test compounds, each compound is evaluated for a biological or pharmacological activity relevant to a disease indication. The compounds that perform best are then selected as lead compounds for further development.

The evaluations can be performed either serially one compound at a time or, preferably, in a high-throughput screening format. Given the starting library and the appropriate assays, it is within the skill of the art to devise high-throughput screening protocols for identifying a stereodynamic mimic as a lead compound.

3. Methods for Synthesizing Stereodynamic Mimic Compounds

In another aspect, the present invention also provides a method of synthesizing stereodynamic mimic compounds. As noted above, a stereodynamic mimic compound may be any compound containing one or more stereodynamic chiral center. In a preferred embodiment, the stereodynamic mimic is a peptide. Such peptides may preferably be synthesized using a solid-phase peptide synthesis (SPPS) method. As will be appreciated by those in the art, the compounds of the invention can be synthesized using standard SPPS methods. For example, using aza-proline instead of proline as indicated and shown in FIGS. 4 and 5 (FIG. 4 shows the synthesis of Fmoc-Aza-Proline which can be incorporated into the method of FIG. 5).

Thus, in one embodiment, methods for making a stereodynamic compound comprising a peptide will include the steps of: providing a stereodynamic amino acid residue suitable for use in a solid-phase peptide synthesis method; performing a solid-phase peptide synthesis method to make the stereodynamic compound.

Figure 4:
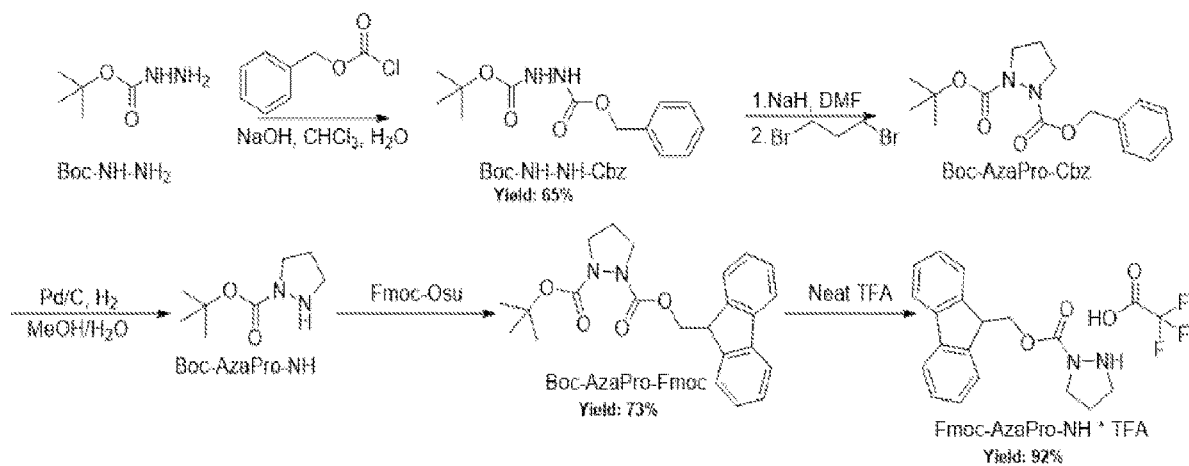
FIG. 4 shows an exemplary synthetic scheme for Glyx-1 and Glyx-2.

FIG. 4 shows an exemplary method of synthesizing a stereodynamic amino acid residue suitable for use in a solid-phase peptide synthesis method. In this case, the stereodynamic amino acid is proline. However, any natural or unnatural amino acid may be similarly used so long as it has a chiral α-carbon.

Figure 5:
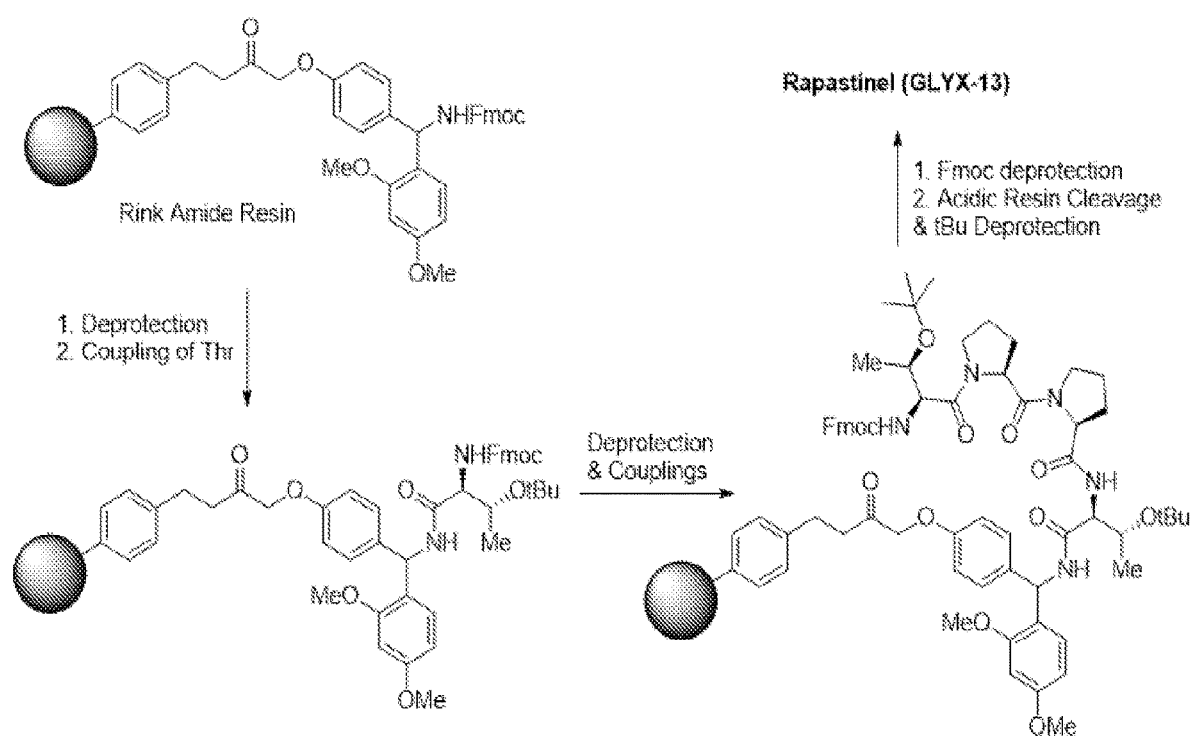
FIG. 5 shows an exemplary synthetic scheme for solid phase peptide synthesis of Rapastinel.

FIG. 5 shows an exemplary solid-phase synthesis method for incorporating one or more stereodynamic amino acid residue(s) into a peptide.

The following examples further illustrate the various aspects of the present invention.

4. Formulation and Dosing

The compounds of the present invention can be formulated with one or more pharmaceutical carriers and/or excipients, in a variety of ways, depending on the administration route, and can be dosed as single dosage units once per time period (e.g. once a week, once a month, twice a month, etc.) or as a daily dosage amount. Particular reference is made to www.clinicaltrials.gov, that outlines a number of different Glyx-13 clinical trials, the dosages, formulations and dosing regimens, all of which are expressly incorporated herein by reference.

In one embodiment, the compounds of the invention are formulated for oral administration, including as liquids or solids such as tablets, capsules and the like. In this embodiment, carriers such as fillers or extenders (including, but not limited to, starches, sugars such as lactose, glucose, mannitol, etc.), binders (including but not limited to starches, carboxymethylcellulose, alginates, etc.), disintegration agents (including but not limited to agar, calcium carbonate, etc.), can all be used, including flavoring agents as appropriate.

In one embodiment, the compounds of the invention are formulated in a liquid dosage form for injections, including intravenous, intramuscular or subcutaneous dosages. These formulations can also include buffers, carriers, sugars and other carbohydrates such as mannitol, etc.

In some embodiments, the compounds of the invention are formulated for mucosal delivery, such as suppositories, or topical administration, such as creams.

5. Treatment

In one aspect of the invention, the compounds of the invention (Glyx-1, Glyx-2 and/or Glyx-3) are used to treat a neurological condition, similar to the neurological conditions treatable by Glyx-13, as is generally outlined in U.S. Pat. No. 8,492,340, hereby expressly incorporated by reference in its entirety.

In some embodiments, the neurological condition is a depression condition. A variety of depression conditions can be treated without some typical side effects (for example, without affecting behavior or motor coordination, and without inducing or promoting seizure activity). Exemplary depression conditions that are expected to be treated according to this aspect of the invention include, but are not limited to, major depressive disorder, dysthymic disorder, psychotic depression, postpartum depression, premenstrual syndrome, premenstrual dysphoric disorder, seasonal affective disorder (SAD), anxiety, mood disorder, depressions caused by chronic medical conditions such as cancer or chronic pain, chemotherapy, chronic stress, post traumatic stress disorders, risk of suicide, and bipolar disorder (or manic depressive disorder). It should be understood that depression caused by bipolar disorder may be referred to as bipolar depression. In addition, patients suffering from any form of depression often experience anxiety. Various symptoms associated with anxiety include fear, panic, heart palpitations, shortness of breath, fatigue, nausea, and headaches among others. It is expected that the methods of the present condition can be used to treat anxiety or any of the symptoms thereof.

Other neurological conditions that can be treated using the compounds of the invention, including, but are not limited to, a learning disorder, autistic disorder, attention-deficit hyperactivity disorder, Tourette's syndrome, phobia, post-traumatic stress disorder, dementia, AIDS dementia, Alzheimer's disease, Parkinson's disease, Huntington's disease, spasticity, myoclonus, muscle spasm, bipolar disorder, a substance abuse disorder, urinary incontinence, and schizophrenia.

In some embodiments, patients who have refractory depression or those that are treatment resistant are treated using the compounds of the invention. That is, patients whose depression disorder has not responded to adequate courses of other antidepressant compounds or therapeutics.

In these embodiments, dosages from about 1 mg/kg, 5 mg/kg and 10 mg/kg can be given to patients.

EXAMPLES

Example 1: Design of Glyx-13 Stereodynamic Mimics

As noted above, Glyxins are a class of compounds that have partial agonist activity against the glycine site of the NMDA receptor. This receptor is involved in many cognitive functions, such as learning, memory, depression, and schizophrenia. The structure of these Glyxins was derived from the sequence of the hyper variable light chain of the monoclonal antibody B6B21. One of the more effective Glyxins, Glyx-13 is the focus of this example.

Glyx-13 is a long lasting drug with high anti-depressant activity, but no central nervous system related side-effects. It is currently being fast tracked by the FDA as a possible adjunctive therapy for resistant major depressive disorder. Glyx-13 is of interest because many other glycine site NMDA receptor agonists cause serious neurological side effects, such as schizophrenic tendencies. While Glyx-13 is a great drug candidate, it does have one problem—it has to be injected in order to be administered. This is because of the poor bioavailability and enzymatic degradation it undergoes in the body.

Glyx-13 is a proline rich peptide, hence, it makes an excellent candidate for stereomimicry optimization. By substituting prolines with azaprolines, the peptide can be made more stereodynamic. This aza-proline will mimic a stereocenter, and possibly increase the bioavailability and receptor binding activity of Glyx-13. Previous work by the inventor has shown that the AzaPro-Pro sequence is stereodynamic and can mimic both L and D-amino acids readily. By substituting the prolines individually with azaprolines, two stereodynamic mmics of the Glyx-13, namaly, Glyx-1 and Glyx-2 were created (FIG. 3).

Example 2: Synthesis of azaPro Residue Suitable for Use in SPPS

To facilitate solid-phase peptide synthesis of Glyx-1 and Glyx-2, the inventor has devised a blocked azaPro residues in the form of Boc-AzaPro-NH and Boc-AzaPro-Fmoc. FIG. 4 shows the full synthesis of the Fmoc-AzaPro-NH that was used in the peptide synthesis. The Boc-AzaPro-NH and Boc-AzaPro-Fmoc were both purified using silica gel column chromatography while the other compounds were all purified using extraction. The Fmoc-AzaPro-NH was purified through precipitation in cold ether and the mass was verified by mass spectrometry.

Example 3: SPPS of Glyx-13, Glyx-1 and Glyx-2

Once the aza-proline was synthesized, Glyx-13, Glyx-1, and Glyx-2 were synthesized using solid phase peptide synthesis methods, outlined in FIG. 5. The aza-proline coupling required an extra step where the acyl chloride of the Fmoc-AzaPro was synthesized in order to make the coupling reaction more effective. The resin was charged twice for 12 hours with this coupling solution and then regular solid phase peptide synthesis was used to finish making Glyx-1 and Glyx-2. The masses of the Glyx-13, Glyx-1, and Glyx-2 were confirmed using high resolution mass spectroscopy, with an error of less than 5 ppm. All compounds were purified through precipitation in cold ether and carried on to use in the neurite outgrowth assay in order to gather preliminary data.

Example 4: Evaluation of Glyx-1 and Glyx-2 Neuronal Protective Activities

Figure 6:
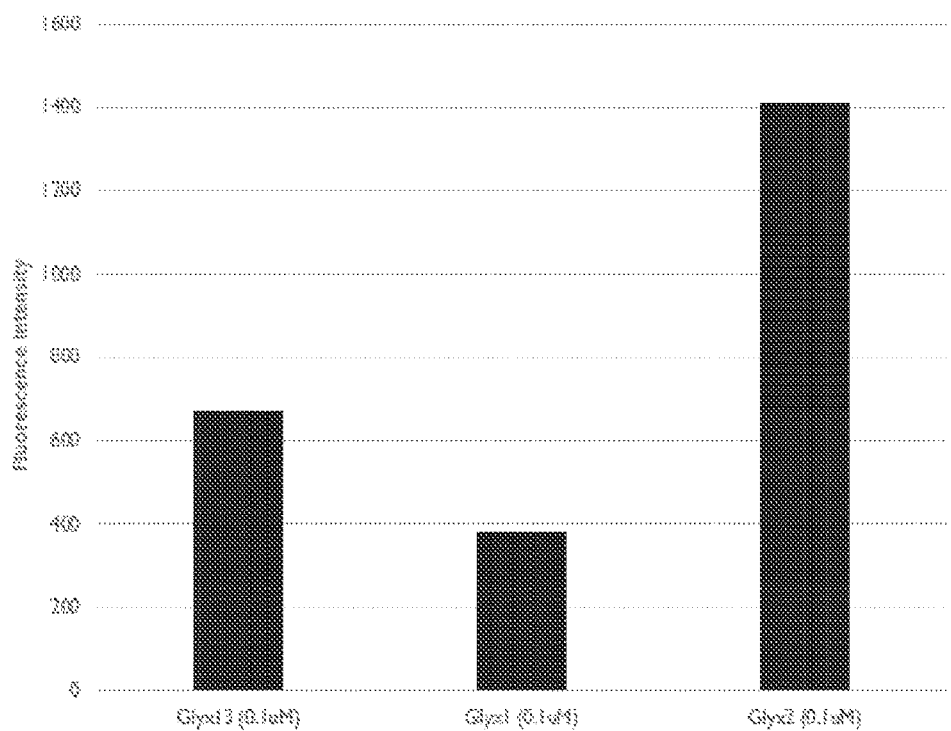
FIG. 6 shows membrane stain (upper panel) and cell viability data (lower panel) from Neurite Outgrowth Assay.
Figure 6:
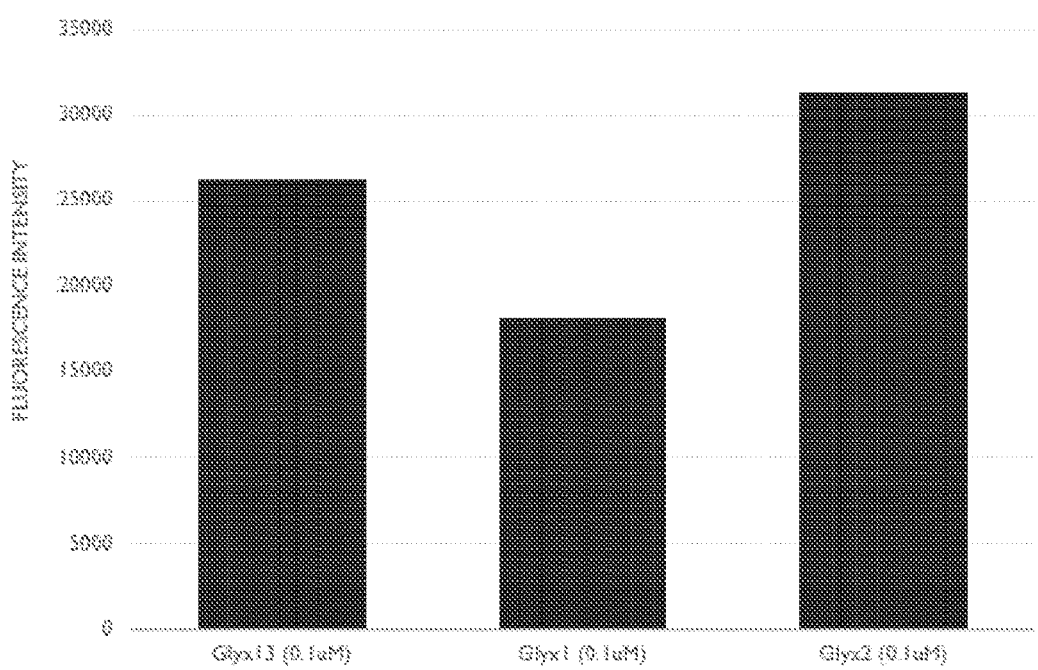

Once the three compounds were synthesized the neurite outgrowth assay was used in order to determine the effectiveness of the aza-proline derivatives in comparison with the Glyx-13. Mouse neuroblastoma cells (Neuro-2a cells) were used in order to measure the increase in neurite growth between untreated cells and those treated with the test compounds. A plate reader assay was used where 9,000 cells/cm$^2$ were treated with the compounds at 0.01, 0.10, and 1.00 μM concentrations for 48 hours. Several controls were used as well, including wells with no cell and compound, cells with no compound (just water), and wells with no cells and water. After treatment with the compounds, the cells were washed in DPBS buffer and treated with cell viability indicator and a membrane stain for 20 minutes before being washed again and treated with a background suppression dye. The plate reader assay was inconclusive for some of the concentrations of the compounds, but the 0.10 μM data is promising. (FIG. 6)

Figure 7:
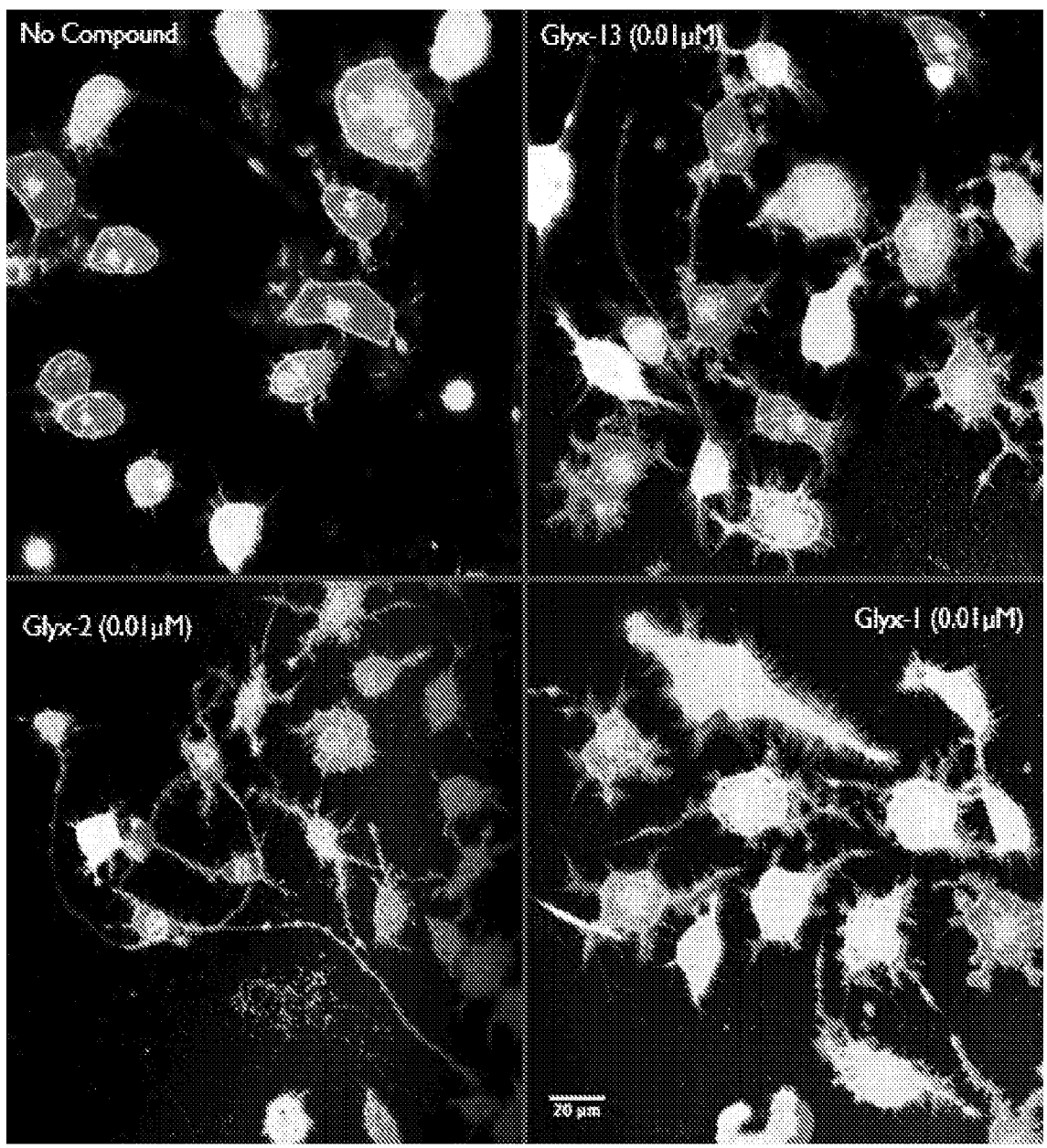
FIG. 7 shows confocal microscope images of neuro-2a cells.

There appears to be a significant increase in the size of the neurites and no significant cell death with treatment of 0.10 μM Glyx-2. Confocal microscopy was used in order to image the neuronal cells to determine, qualitatively, if the Glyx-1 and Glyx-2 were as effective or had a different effect than the Glyx-13. In FIG. 7, there is a significant increase in the number of projections from no treatment to the Glyx-13 compound. This increase is even more noticeable in the Glyx-2 and Glyx-1 images where the projections get larger as well as the dendrites on the cells.

The confocal microscope data seems to indicate that the Glyx-2 compound is significantly more effective than the control compound, Glyx-13. This can be seen in the increase in neuronal projections and dendrite length. This indicates that the incorporation of the aza-proline into the Glyx-13 structure made it more effective, either through increasing the bioavailability or its interaction with the NMDA receptor.

Other proline-rich peptide drugs may also benefit from the above approach by incorporating aza-proline to make them more effective.

While specific embodiments and examples of the present invention are described above, it will be understood that such embodiments are by way of example only and are merely illustrative of but a small number of many possible specific embodiments which can represent applications of the principles of the present invention. Various changes and modifications obvious to one skilled in the art to which the present invention pertains are deemed to be within the spirit, scope and contemplation of the present invention as further defined in the appended claims.

What is claimed is:

1. A method for optimizing a candidate compound containing one or more stable chiral atom, comprising:
   generating a plurality of stereodynamic mimic compounds by replacing one or more of the stable chiral atom with a stereodynamic atom capable of mimicking chirality;
   evaluating each of the stereodynamic mimic compounds for relevant biological activities as compared to those of the compound; and
   selecting those stereodynamic mimic compounds that show more effective biological activities or different pharmacokinetic or metabolic properties and designating said compounds as improved compounds.

2. The method of claim 1, wherein said stereodynamic atom capable of mimicking chirality is N or B.

3. The method of claim 1, wherein said candidate compound is a peptide containing one or more stereogenic amino acid.

4. The method of claim 3, wherein said sterogenic amino acid is proline or a proline mimic.

5. The method of claim 4, wherein said stable chiral atom is an α-carbon of the proline residue and the stereodynamic atom is nitrogen.

6. The method of claim 1, wherein said candidate compound is a Glyxin.

* * * * *